(12) United States Patent
Thomsen et al.

(10) Patent No.: US 7,983,382 B2
(45) Date of Patent: Jul. 19, 2011

(54) SYSTEM AND METHOD FOR MATERIAL SEGMENTATION UTILIZING COMPUTED TOMOGRAPHY SCANS

(75) Inventors: Brian Thomsen, Milwaukee, WI (US); John Lawrence Seamans, Ann Arbor, MI (US)

(73) Assignee: General Electric Company, Schenectady, NY (US)

( * ) Notice: Subject to any disclaimer, the term of this patent is extended or adjusted under 35 U.S.C. 154(b) by 104 days.

(21) Appl. No.: 12/323,929

(22) Filed: Nov. 26, 2008

(65) Prior Publication Data

US 2010/0128844 A1    May 27, 2010

(51) Int. Cl.
*A61B 6/00* (2006.01)
(52) U.S. Cl. .................. 378/5; 378/4; 382/128
(58) Field of Classification Search .............. 378/4, 5, 378/53, 98.9, 98.11
See application file for complete search history.

(56) References Cited

U.S. PATENT DOCUMENTS

| | | | | |
|---|---|---|---|---|
| 4,686,695 A * | 8/1987 | Macovski | ...................... | 378/146 |
| 4,788,706 A * | 11/1988 | Jacobson | ...................... | 378/207 |
| 5,187,658 A * | 2/1993 | Cline et al. | ...................... | 382/128 |
| 6,324,240 B1 * | 11/2001 | Yan et al. | ...................... | 378/4 |
| 6,658,080 B1 * | 12/2003 | Poole et al. | ...................... | 378/4 |
| 7,778,454 B2 * | 8/2010 | Grasruck et al. | ...................... | 382/128 |
| 2003/0142857 A1 * | 7/2003 | Alyassin | ...................... | 382/131 |
| 2004/0028181 A1 * | 2/2004 | Charles, Jr. et al. | ...................... | 378/92 |
| 2004/0101086 A1 * | 5/2004 | Sabol et al. | ...................... | 378/4 |
| 2004/0184574 A1 * | 9/2004 | Wu et al. | ...................... | 378/5 |
| 2004/0223585 A1 * | 11/2004 | Heismann et al. | ...................... | 378/54 |
| 2005/0084069 A1 * | 4/2005 | Du et al. | ...................... | 378/98.9 |
| 2006/0109949 A1 * | 5/2006 | Tkaczyk et al. | ...................... | 378/4 |
| 2007/0092056 A1 * | 4/2007 | Flohr et al. | ...................... | 378/4 |
| 2007/0249933 A1 * | 10/2007 | Krauss | ...................... | 600/425 |
| 2009/0028287 A1 * | 1/2009 | Krauss et al. | ...................... | 378/4 |

OTHER PUBLICATIONS

Santamaria-Pang et al., Automated Liver Lesion Characterization using fast kVp switching Dual Energy Computed Tomography Imaging, Medical Imaging, SPIE, vol. 7624, 2010, pp. 1-10.*
Vega-Higuera et al., Interactive Tissue Separation and Visualization with Dual-Energy Data on the GPU, Medical Imaging, SPIE, vol. 6918, 2008, pp. 1-8.*
Forrest, Wayne, "Dual-energy CT may assist in coronary plaque identification", AuntMinnie.com,, Jan. 15, 2007.

* cited by examiner

*Primary Examiner* — Edward J Glick
*Assistant Examiner* — Alexander H Taningco
(74) *Attorney, Agent, or Firm* — McAndrews, Held & Malloy, Ltd.; Michael A. Dellapenna

(57) ABSTRACT

Certain embodiments provide a radiation analysis system for material segmentation utilizing computed tomography (CT) scans. The radiation analysis system includes an input module configured to input dual energy data. The dual energy scanned data includes first data corresponding to a first parameter and second data corresponding to a second parameter for a given scanned volume. The radiation analysis system also includes a processor configured to generate a scatter plot based on the dual energy data. The first data corresponds to a first axis and the second data corresponds to a second axis. The processor is configured to identify at least one material type based on the scatter plot.

20 Claims, 3 Drawing Sheets

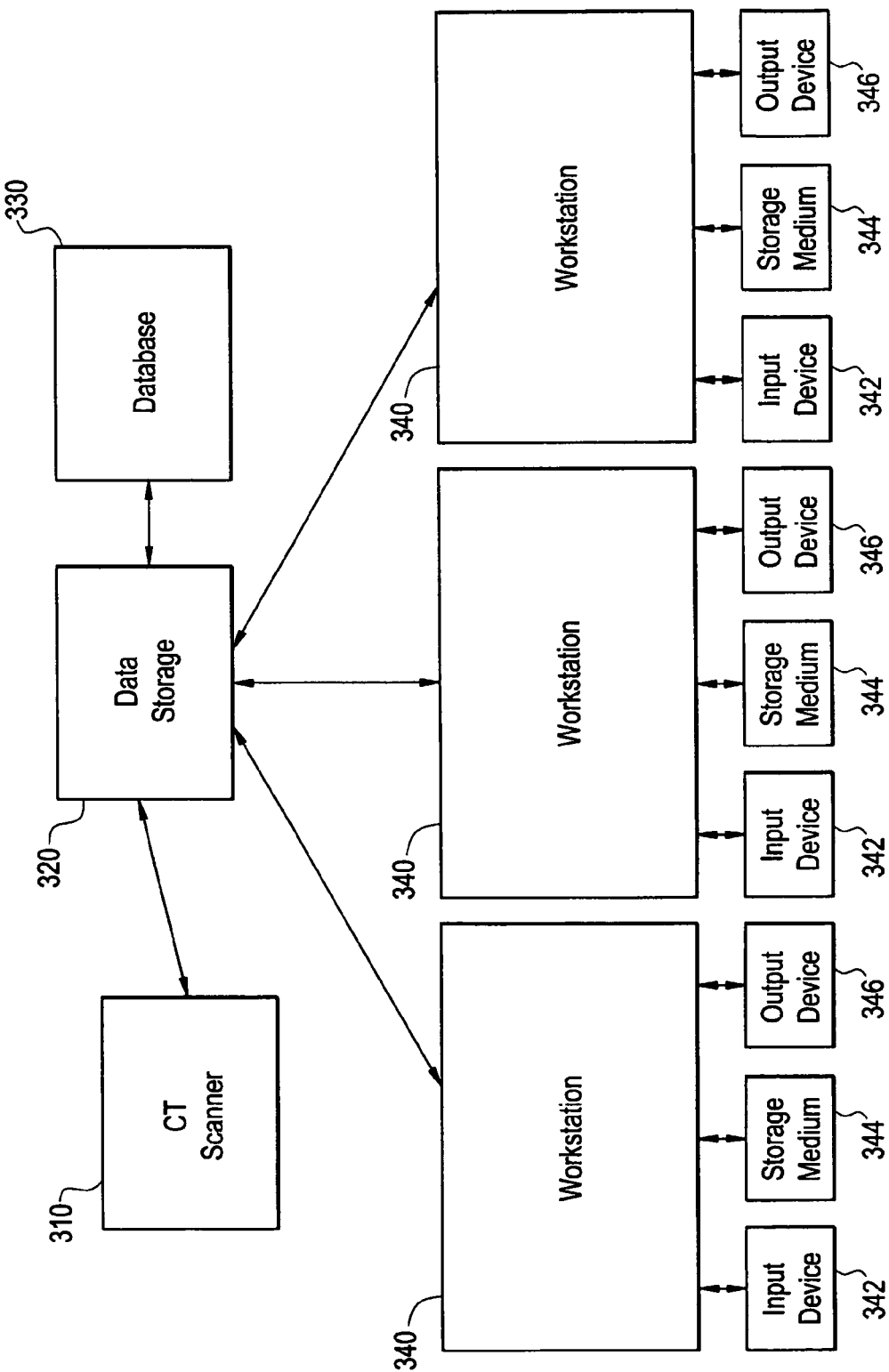

SYSTEM AND METHOD FOR MATERIAL SEGMENTATION UTILIZING COMPUTED TOMOGRAPHY SCANS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Computed tomography (CT) is a medical imaging method. Images from CT scans are generally prepared by combining slices of two-dimensional X-rays to generate a three-dimensional image of a volume. Dual energy CT scanning is performed by scanning a patient at two different energy levels in a sequential or interleaved fashion over the same volume. The two different resulting x-ray spectra used for the scans provides information about the x-ray linear attenuation of the materials contained within the scanned volume.

Such dual energy scans may be used for material segmentation, or to attempt to identify materials in the scanned volume. Currently known techniques for such segmentation, however, do not fully utilize the information potentially available from dual energy scanning. Moreover, such techniques do not include the ability to select arbitrary energy levels at which to identify attenuation levels. Further, such techniques may lack distinctness and/or accuracy in their segmentation of materials because, for example, they are based off a polychromatic spectrum, and include the combined effects of all energies in that spectrum.

BRIEF SUMMARY OF THE INVENTION

Certain embodiments of the present invention provide methods and systems for performing material segmentation utilizing computed tomography (CT) scans.

Certain embodiments provide a radiation analysis system for material segmentation. The radiation analysis system includes an input module configured to input dual energy data. The dual energy scanned data includes first data corresponding to a first parameter and second data corresponding to a second parameter for a given scanned volume. The radiation analysis system also includes a processor configured to generate a scatter plot based on the dual energy data. The first data corresponds to a first axis and the second data corresponds to a second axis. The processor is configured to identify at least one material type based on the scatter plot.

In certain embodiments, the radiation analysis system includes a display module configured to display an image representative of scanned anatomy, and a user selection module configured to allow a user to select a portion of the image for which the dual energy projection data will be input into the input module. In certain embodiments, the processor is configured to identify a plurality of material types based on clusters located in the scatter plot. The first data may include Hounsfield unit values corresponding to a first energy level, and the second data may include Hounsfield unit values corresponding to a second energy level. In certain embodiments, the radiation analysis system includes a display module configured to display an image representative of scanned anatomy including the at least one material type identified based on the scatter plot for at least a portion of the image, and/or to display the scatter plot. The radiation analysis system may also include a parameter selection module configured to permit a user to select the first and second parameters.

Certain embodiments provide a method for material segmentation of a computed tomography (CT) scanned volume. The method includes the step of identifying first data associated with a first parameter of a CT scan, and identifying second data associated with a second parameter of the CT scan. The method further includes generating a scatter plot based on the first and second data, wherein the first data corresponds to a first axis and the second data corresponds to a second axis. The method also includes identifying a material type based on the scatter plot.

Certain embodiments provide a computer-readable storage medium including a set of instructions for execution on a processing device and associated processing logic. The set of instructions include an input routine that allows the value of at least first data corresponding to a first parameter of a CT scan and second data corresponding to a second parameter of the CT scan to be input. The set of instructions also includes a processing routine configured to generate a scatter plot based on the first and second data, wherein the first data corresponds to a first axis and the second data corresponds to a second axis. The processing routine is configured to identify at least one material type based on the scatter plot.

BRIEF DESCRIPTION OF SEVERAL VIEWS OF THE DRAWINGS

FIG. 3 illustrates a radiation analysis system in accordance with an embodiment of the present invention.

Figure 1:
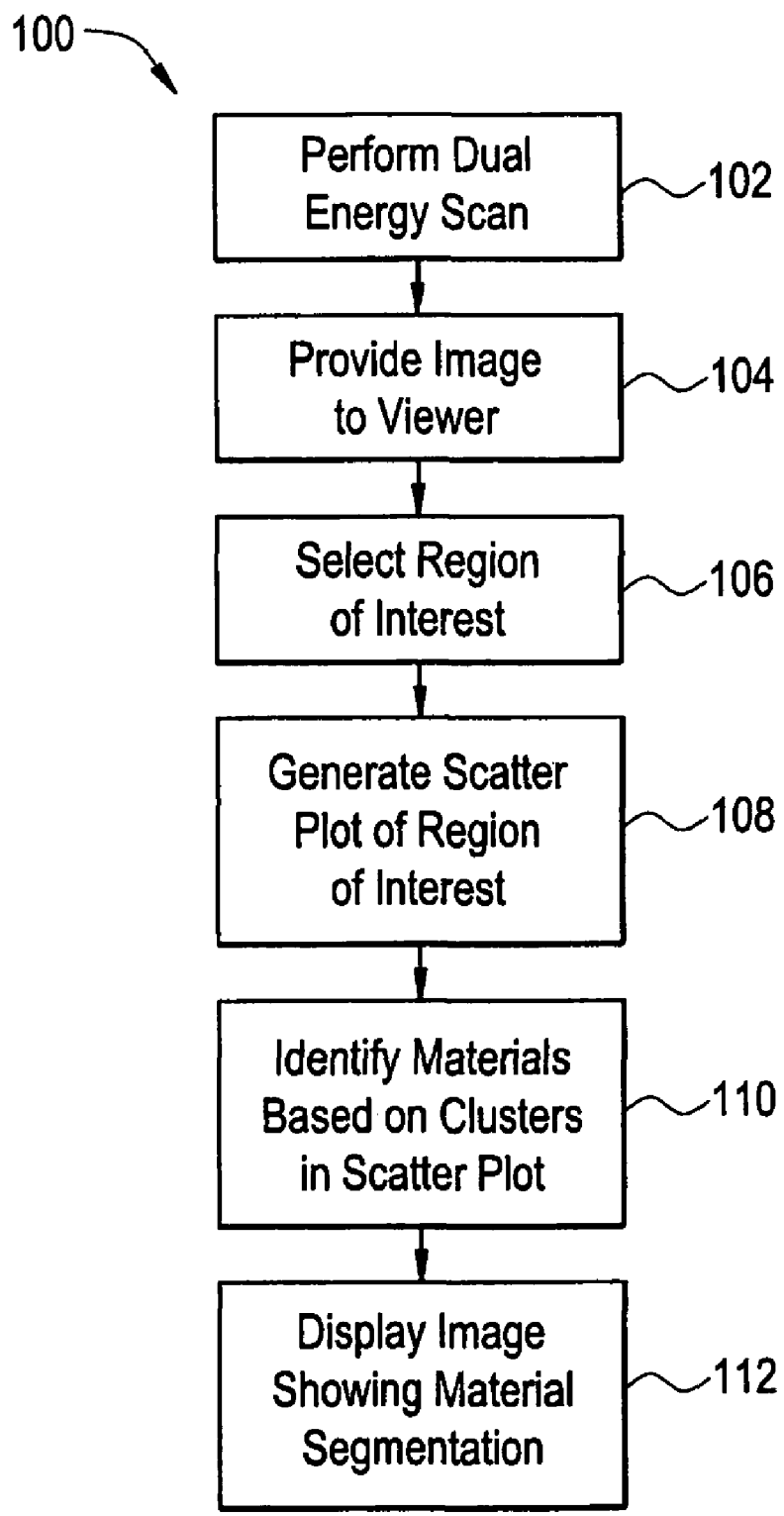
FIG. 1 shows a flow diagram for a method for material segmentation based on a dual energy CT scan according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain aspects of the present invention provide an automated method of material identification and/or segmentation from computed tomography (CT) scans taken at multiple energy levels.

FIG. 1 shows a flow diagram for a method 100 for material segmentation based on a multiple energy CT scan according to an embodiment of the present invention.

At step 102, a CT scan is taken at multiple energy levels over a given volume of a patient. The scan may be performed at two energy levels (also known as dual energy scanning) using a dual energy CT scanner. For example, a patient may be scanned at two different levels in a rapid sequential or interleaved fashion over the same volume. The two scans thus provide information about x-ray attenuation for the given volume at two different energy levels. As an example, the scan may be performed under a first energy spectrum corresponding to about 80 kVp and a second energy spectrum corresponding to about 140 kVp. The dual energy scan thus provides information for determining various parameters relating to the scanned volume. For example, the dual energy scan may provide Hounsfield unit values (a measure of attenuation) for each kVp energy level for a given voxel (volume element). Using a process called material basis decomposition, the attenuation characteristics of each voxel in the scan can be decomposed into a linear combination of the characteristics of two basis materials (for example, water and iodine). In these images, each pixel is in units of density (mg/cc) and are called material density images. Another representation of this same information is in the form of two monochromatic images. Monochromatic images have pixel values in units of Hounsfield units, however they differ from traditional CT images in that these images show the effects of attenuations as if the object were scanned by a monochromatic tube source rather than a polychromatic source. As an example, the original scan may have been taken with tube voltages of 80 kVp and 140 kVp. However, through material basis decomposition, a monochromatic image at, for example, 70 keV may be generated. The monochromatic images remove beam hardening effects and provide a way for users to more clearly see the attenuation characteristics of each material in the scanned object.

At step 104, an image representing the scanned volume is provided to a viewer. The image may be provided on, for example, the monitor of a workstation. Further, the viewer may be able to select among various viewpoints from which to view the image. For example, the viewer may be able to select a view showing a top view of a given slice through the scanned volume, or various side elevation views made up of a composite of slices through the scanned volume. Alternatively, a perspective view constructed from the scan may be presented.

At step 106, the viewer optionally selects a region of interest from the image provided to the viewer. For instance, a viewer may use a mouse or other input device associated with the workstation at which the image is being displayed to select a portion of the scanned volume as a region of interest. As an example, the viewer may be examining an image generated by the CT scan of a patient's head. The image may contain a portion of interest to the viewer, for example, an area that may appear to be potentially a cyst or tumor. The viewer may then select that particular region as a region of interest, for which the viewer would like a more detailed analysis of the materials present to be performed. In certain embodiments, the viewer may select first and second parameters which will be utilized to generate a scatter plot. For example, the viewer may select a first parameter to be Hounsfield unit values at a monochromatic energy level selected from a range of approximately 40-70 keV to correspond to a first axis of the scatter plot, and a second parameter to be Hounsfield unit values at a monochromatic energy level selected from a range of approximately 100-140 keV to correspond to a second axis of the scatter plot. Thus, as an example, a viewer may select a scatter plot to have an x-axis corresponding to a monochromatic energy level of 70 keV and a y-axis corresponding to a monochromatic energy level of 140 keV.

At step 108, a scatter plot is generated for the region of interest. This scatter plot may be generated, for example, by a general purpose computer performing an algorithm on the data provided by the dual energy scan. As one example, the data provided for the selected volumetric region of interest may include Hounsfield unit values corresponding to each of two scanned energy levels for each voxel of the given volume. Alternatively, there may be other properties made available through the dual energy data such as Hounsfield unit values at different monochromatic energy levels or material density values across basis materials (such as water and iodine). For example, the data may include the Hounsfield value for each voxel at a first monochromatic energy level (for example, about 70 keV) as well as the Hounsfield value for that voxel at a second monochromatic energy level (for example, about 140 keV). This data may then be used to create a scatter plot. For example, the x-axis of the scatter plot may correspond to the attenuation (represented by Hounsfield units) at 70 keV, and the y-axis may correspond to the attenuation (represented by Hounsfield units) at 140 keV. Thus, for each voxel of the volume of interest, a data point is defined on the scatter plot by that voxel's attenuation at 70 keV (location along the x-axis) and that voxel's attenuation at 140 keV (location along the y-axis). Further, the energy values selected for the scatter plot may be selected from other energy levels. For example, CT images may be generated at arbitrary energy levels in image space, allowing a user to select a preferred energy level for a given anatomy, material, or other consideration. Such projection based approaches may not be possible using data acquired with some known two-tube, two-detector scanners. Additionally, data for different and/or additional energy levels may be used. Density values in material density images may also be used in these scatter plots. For example, a voxel's decomposition in water density could be the x-axis value, and the voxel's decomposition in iodine density could be the y-axis value. As an additional example, a three-dimensional scatter plot having axes corresponding to measurements taken at three energy levels may be created.

Figure 2:
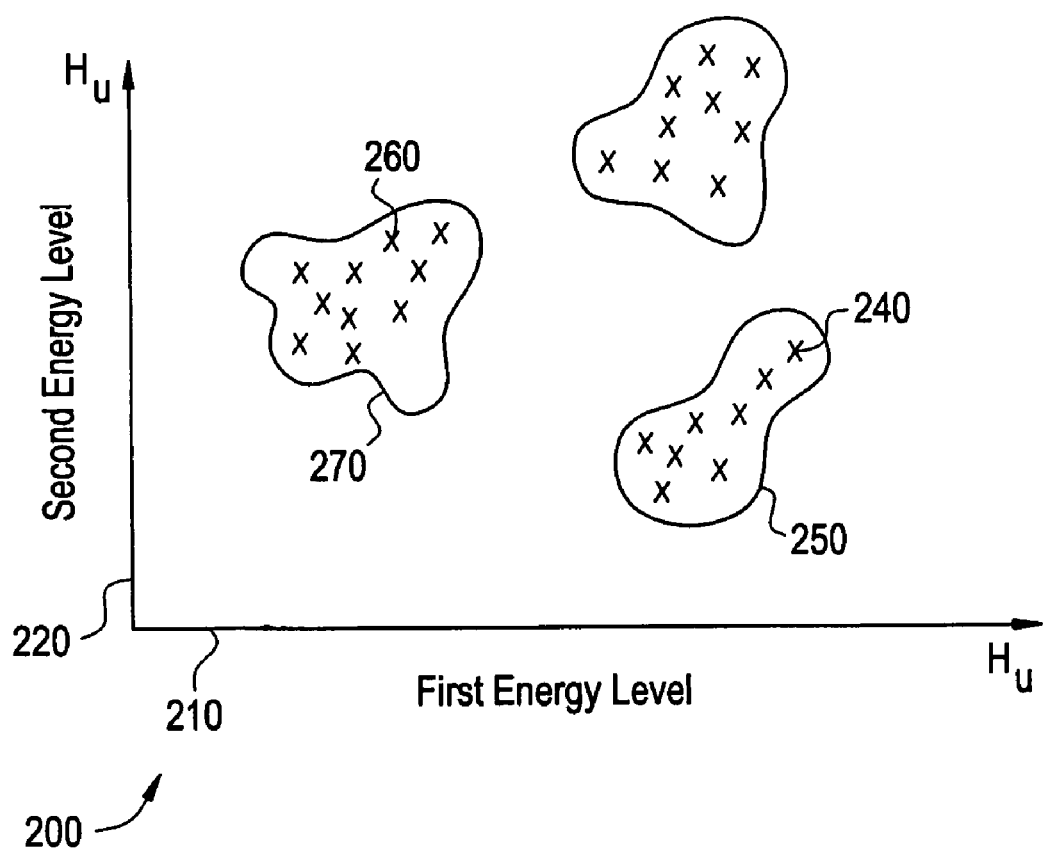
FIG. 2 illustrates an example of a scatter plot formed in accordance with an embodiment of the present invention.

FIG. 2 illustrates an example of a scatter plot 200 formed in accordance with an embodiment of the present invention. The scatter plot 200 illustrated in FIG. 2 is not intended to represent any specific material and/or energy levels, but is rather for illustrative purposes only. The scatter plot 200 includes an x-axis 210 and a y-axis 220. In the illustrated embodiment, the x-axis 210 corresponds to the Hounsfield unit value at a first energy level, and the y-axis 220 corresponds to the Hounsfield unit value at a second energy level. A given voxel of a CT scan will have a known Hounsfield unit value at each of the energy levels and thus can be plotted on the scatter plot 200. Each voxel will have a corresponding data point on the scatter plot. These data points can be analyzed with a clustering algorithm and viewed as parts of clusters (as will further be described in connection with step 110 below). For example, in the illustrated embodiment, data point 240 on the scatter plot 200 may be associated with cluster 250, and data point 260 may be associated with cluster 270. A 'fuzzy membership' can be defined in cases where there is ambiguity. That is, if a voxel's location in the scatter plot does not clearly belong to a cluster of other like materials, it may be defined as having some fractional membership to a number of different clusters. As further described below, a material type may be identified for each cluster. Thus, data point 240 will be identified as being composed of the material associated with cluster 250 based on the attenuation values.

At step 110, material segmentation is performed based on the scatter plot. For example, data points (each corresponding to a voxel of the selected image) may form clusters on the scatter plot. Using a clustering algorithm, the data points may be grouped into clusters. Various clustering algorithms may be used. For example, clustering techniques include K-means clustering, Fuzzy C-means clustering, and QT clustering. As will be appreciated by those skilled in the art, different trade-offs between these algorithms, such as computational complexity, reproducibility of results, and having to know the number of clusters prior to the analyses may be factors to be considered when selecting the type of algorithm to be employed. Then, based on the attenuation values for that cluster at each energy value, a material type is identified, based on materials known to have attenuation values at the given energy levels corresponding to the location of that particular cluster. For example, the relationship between the Hounsfield unit value for a given voxel and the monochromatic energy level used in generating that voxel helps identify a class of materials. The class of materials may be further better identified by knowing the relationship between the Hounsfield unit value for the same voxel at a different energy level. By examining the change of the Hounsfield unit value as a function of changing monochromatic energy level, the material may be more specifically isolated and identified. By using such a projection-based reconstruction of monochromatic images to create the scatter plot, the clusters formed will be more distinct than if data points were identified using combined effects of multiple energies as is the case under a polychromatic spectrum. Also, this technique may also provide the capability to allow for optimal selection of energy values to be used on the axes of the scatter plot. For example, a given material that may be particularly of interest to a viewer may have a more distinct attenuation level at a given energy level (or levels). To help identify that material, the given energy level (or levels) corresponding to the more distinct attenuation level could be selected to help improve identification.

At step 112, an image is presented to the viewer displaying the results of the material segmentation. The image may be presented on a display module displaying an image representative of the scanned anatomy showing portions of the selected volume differentiated based on the scatter plot. The display module may be a monitor associated with a computer workstation being used by the viewer. For example, the image may be created by assigning a specific color to each of the materials identified with clusters formed in the scatter plot. Then, each voxel that falls within a cluster is assigned that color in the image presented to the viewer. Returning to the example illustrated in FIG. 2, the voxel corresponding to data point 240 could be identified as being the material corresponding to cluster 250, and, on the image presented to the viewer, that voxel could be displayed as the color associated with that particular material. Thus, for example, a viewer could determine which portions of the image were bone, muscle and/or soft tissue, fat, calcium, blood, or iodine or other material introduced for contrast. Further, cysts and/or tumors may be more easily identifiable on the presented image. For example, returning to the example of the viewer that selected a head scan from above, the image presented to the viewer could present the materials for the different portions of the selected volume, allowing the viewer to more accurately diagnose the presence of a cyst and/or tumor that was initially suspected as being potentially located in the selected volume. Alternatively or additionally, the viewer may also be presented with a display of the scatter plot itself, allowing more in-depth study of how the particular materials were identified.

One or more of the steps of the method 100 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps, and/or perform the steps in a different order than the order listed, and/or combine certain of the steps listed above. For example, some steps may not be performed in certain embodiments of the present invention. As a further example, certain steps may be performed in a different temporal order, including simultaneously, than listed above.

FIG. 3 illustrates a radiation analysis system 300 in accordance with an embodiment of the present invention. Certain embodiments of the radiation estimation described above may be implemented in a radiation analysis system, such as the system 300 of FIG. 3. In certain embodiments, a radiation analysis may be viewed and/or constructed using a system such as system 300 including at least one computed tomography (CT) scanner 310, at least one data storage 320, at least one database 330, and at least one workstation 340. For example, while three workstations 340 are illustrated in system 300, a larger or smaller number of workstations 340 can be used in accordance with embodiments of the presently described technology. In addition, while one data storage 320 is illustrated in system 300, system 300 can include more than one data storage 320. For example, each of a plurality of entities (such as remote data storage facilities, hospitals or clinics) can each include one or more data stores 320 in communication with one or more workstations 340. In addition, while one database 330 is illustrated in system 300, system 300 can include more than one database 330. In certain embodiments, database 330 may be a part of, or replaced by, data storage 320. In addition, while one CT scanner 310 is illustrated in system 300, system 300 can include more than one CT scanner 310. In certain embodiments, the radiation analysis system is part of and/or used in conjunction with a larger clinical information system which may include, for example, hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR).

As illustrated in system 300, one or more workstations 340 can be in communication with at least one other workstation 340 and/or at least one data storage 320. Workstations 340 can be located in a single physical location or in a plurality of locations. Workstations 340 can be connected to and communicate via one or more networks.

Workstations 340 and/or CT scanners 310 can be directly attached to one or more data stores 320 and/or communicate with data storage 320 via one or more networks. Each workstation 340 can be implemented using a specialized or general-purpose computer executing a computer program for carrying out the processes described herein. Workstations 340 can be personal computers or host attached terminals, for example. If workstations 340 are personal computers, the processing described herein can be shared by one or more data stores 320 and a workstation 340 by providing an applet to workstation 340, for example.

In certain embodiments, the CT scanner 310 may comprise an input module that provides data from a CT scan to a processor for further analysis. In certain embodiments, the data storage 320 and/or workstation 340 may comprise an input module that provides data from a CT scan to a processor for further analysis. For example, additional manipulation may be performed on the data obtained from the CT scan to generate additional or modified data to be input to a processor for generation of a scatter plot. As an example, projections may be performed to generate data for energy levels at which a volume of anatomy was not scanned.

Workstations 340 include an input device 342, an output device 346 and a storage medium 344. For example, workstations 340 can include a mouse, stylus, microphone and/or keyboard as an input device. In certain embodiments, a workstation 340 or a component thereof may comprise a user selection module configured to allow selection of at least one region of interest from a CT scan being viewed. As an example, a user may utilize a mouse to select points on a screen defining a boundary of a region of interest for which material segmentation is desired. In certain embodiments, workstation 340 or a component thereof may comprise a parameter selection module configured to allow selection of the parameters associated with the scatter plot. For example, a user may utilize a keyboard to input two energy levels for which the user would like the scatter plot to be generated.

Workstations 340 can include a computer monitor, liquid crystal display ("LCD") screen, printer and/or speaker as an output device. In certain embodiments, a workstation 340 or a component thereof may comprise a display module configured to display at least one of a CT scan image, a scan image including portions identified by material type based on the scatter plot, and/or a scatter plot created from a multiple energy scan. As an example, the output device 346 of the workstation 340 may comprise a display screen that displays CT scan images and/or scatter plots.

Storage medium 344 of workstations 340 is, for example, a computer-readable memory. For example, storage medium 344 can include a computer hard drive, a compact disc ("CD") drive, a USB thumb drive, or any other type of memory capable of storing one or more computer software applications. Storage medium 344 can be included in workstations 340 or physically remote from workstations 340. For example, storage medium 344 can be accessible by workstations 340 through a wired or wireless network connection.

Storage medium 344 includes a set of instructions for a computer. The set of instructions includes one or more routines capable of being run or performed by workstations 340. The set of instructions can be embodied in one or more software applications or in computer code.

Data storage 320 can be implemented using a variety of devices for storing electronic information such as a file transfer protocol ("FTP") server, for example. Data storage 320 includes electronic data. For example, data storage 320 can store patient exam images and/or other information, electronic medical records, patient orders, etc., for a plurality of patients. Data storage 320 may include and/or be in communication with one or more clinical information systems, for example. In certain embodiments, data storage 320 comprises a processor configured to create a scatter plot based on attenuations at multiple energy levels for a selected scan volume, and to identify material types based on clusters identified in the scatter plot. In certain embodiments, data storage 320 comprises an output module configured to provide the database module 330 with data from the original scan, and/or scatter plots and/or images created utilizing information on identified materials based on the scatter plots. Database 330 may be integrated with data storage 320, or may be implemented separately and/or remotely. For example, database 330 can be accessible by data storage 320 through a wired or wireless network connection.

Communication between workstations 340 and/or CT scanners 310 and/or data storage 320 and/or database 330 can be via any one or more types of known networks including a local area network ("LAN"), a wide area network ("WAN"), an intranet, or a global network (for example, Internet). For example, any two of workstations 340 and data stores 320 can be coupled to one another through multiple networks (for example, intranet and Internet) so that not all components of system 300 are required to be coupled to one another through the same network.

Any workstations 340 and/or data stores 320 and/or databases 330 and/or CT scanners 310 can be connected to a network or one another in a wired or wireless fashion. In an example embodiment, workstations 340 and data store 320 communicate via the Internet and each workstation 340 executes a user interface application to directly connect to data store 320. In another embodiment, workstation 340 can execute a web browser to contact data store 320. Alternatively, workstation 340 can be implemented using a device programmed primarily for accessing data store 320.

Data storage 320 can be implemented using a server operating in response to a computer program stored in a storage medium accessible by the server. Data storage 320 can operate as a network server (often referred to as a web server) to communicate with workstations 340. Data storage 320 can handle sending and receiving information to and from workstations 340 and can perform associated tasks. Data storage 340 can also include a firewall to prevent unauthorized access and enforce any limitations on authorized access.

Data store 320 can also operate as an application server. Data store 320 can execute one or more application programs to provide access to the data repository located on data store 320. Processing can be shared by data store 320 and workstations 340 by providing an application (for example, a java applet). Alternatively, data store 320 can include a standalone software application for performing a portion of the processing described herein. It is to be understood that separate servers may be used to implement the network server functions and the application server functions. Alternatively, the network server, firewall and the application server can be implemented by a single server executing computer programs to perform the requisite functions.

The storage device located at data storage 320 can be implemented using a variety of devices for storing electronic information such as an FTP server. It is understood that the storage device can be implemented using memory contained in data store 320 or it may be a separate physical device. The storage device can include a variety of information including a data warehouse containing data such as patient medical data, for example.

Data storage 320 can also operate as a database server and coordinate access to application data including data stored on the storage device. Data storage 320 can be physically stored as a single database with access restricted based on user characteristics or it can be physically stored in a variety of databases.

In certain embodiments of a radiation analysis system described herein, a CT scanner could input data including attenuation levels resulting from a scan of a given volume, and a processor would generate a scatter plot of, for example, attenuation levels at a first energy level versus attenuation levels at a second energy level. The processor would then identify materials for different portions of the given volume based on the scatter plots. Further, in certain embodiments, an output module could provide a generated image providing identification of the materials present in different portions of the scanned volume.

Thus, certain embodiments provide a technical effect of improved material segmentation, and/or improved material identification, and/or providing a more complete use of information available from dual energy scans.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

For example, certain embodiments provide a computer-readable storage medium including a set of instructions for execution on a processing device and associated processing logic. The set of instructions include an input routine that allows the value of first data corresponding to a first parameter of a CT scan and second data corresponding to a second parameter of the CT scan to be input. The set of instructions also includes a processing routine configured to generate a scatter plot based on the first and second data, wherein the first data corresponds to a first axis and the second data corresponds to a second axis. The processing routine is configured to identify at least one material type based on the scatter plot. In certain embodiments, the set of instructions may include a user interface routine configured to provide a user with the option to select a portion of an image representing scanned anatomy for which the scatter plot will be generated. Additionally or alternatively, the processing routing may be configured to identify a plurality of material types based on clusters identified in the scatter plot. Further, the first data may include Hounsfield unit values corresponding to a first energy level, and the second data may include Hounsfield unit values corresponding to a second energy level. Also, the set of instruction may include a display routine configured to allow displaying an image representative of scanned anatomy including at least one material type identified based on the scatter plot for at lest a portion of the image. In certain embodiments, the set of instructions may also include a parameter selection routine configured to allow a user to select the first and second parameters.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A radiation analysis system for material segmentation, said radiation analysis system comprising:
an input module configured to input first computed tomography (CT) data and generate second CT data from said first CT data, said first CT data being obtained from a polychromatic scan, said second CT data comprising first data corresponding to a first parameter and second data corresponding to a second parameter for a given volume, wherein said first parameter and said second parameter correspond to projection-based reconstructions of monochromatic images showing effects of attenuation for an object as if the object were scanned by a monochromatic source instead of a polychromatic source; and
a processor configured to generate a scatter plot based on said second CT data, wherein said first data corresponds to a first axis and said second data corresponds to a second axis, said processor configured to identify at least one material type based on said scatter plot.

2. The radiation analysis system of claim 1 further comprising:

a display module configured to display an image representative of anatomy scanned by a computed tomography scanner; and
a user selection module configured to allow a user to select a portion of said image for which said first CT data will be input into said input module.

3. The radiation analysis system of claim 1 wherein said processor is configured to identify a plurality of material types utilizing clustering techniques based on clusters located on said scatter plot.

4. The radiation analysis system of claim 1 wherein said first data comprises Hounsfield unit values corresponding to a first energy level, and said second data comprises Hounsfield unit values corresponding to a second energy level.

5. The radiation analysis system of claim 4 wherein said first energy level corresponds to a monochromatic energy within the range from about 40 keV to about 70 keV, and said second energy level corresponds to a monchromatic energy within the range from about 100 keV to about 140 keV.

6. The radiation analysis system of claim 1 further comprising a display module configured to display an image representative of scanned anatomy comprising said at least one material type identified based on said scatter plot for at least a portion of said image.

7. The radiation analysis system of claim 1 further comprising a display module configured to display said scatter plot.

8. The radiation analysis system of claim 1 comprising a parameter selection module configured to permit a user to select said first and second parameters.

9. A method for material segmentation of a computed tomography (CT) scanned volume, the method comprising:
identifying first data associated with a first parameter of a CT scan, wherein said first parameter corresponds to a projection-based reconstruction of monochromatic images generated from data obtained from a polychromatic scan, said projection-based reconstruction showing effects of attenuation for an object as if the object were scanned by a monochromatic source instead of a polychromatic source;
identifying second data associated with a second parameter of said CT scan, wherein said second parameter corresponds to a projection-based reconstruction of monochromatic images generated from data obtained from a polychromatic scan, said projection-based reconstruction showing effects of attenuation for an object as if the object were scanned by a monochromatic source instead of a polychromatic source;
generating a scatter plot based on said first and second data, wherein said first data corresponds to a first axis and said second data corresponds to a second axis; and
identifying a material type based on said scatter plot.

10. The method of claim 9 further comprising:
displaying an image representative of anatomy scanned by a CT scanner; and
selecting a portion of said image for which said scatter plot will be generated.

11. The method of claim 9 wherein said identifying a material type comprises identifying a plurality of material types based on clusters identified in said scatter plot.

12. The method of claim 9 wherein said first data comprises Hounsfield unit values corresponding to a first energy level, and said second data comprises Hounsfield unit values corresponding to a second energy level.

13. The method of claim 9 further comprising displaying an image representative of scanned anatomy including at least one material type identified based on said scatter plot for at least a portion of said image.

14. The method of claim 9 further comprising selecting said first and second parameters.

15. A computer-readable storage medium including a set of instructions for execution on a processing device and associate processing logic, the set of instructions comprising:
an input routine that allows first computed tomography (CT) data to be input and second CT data to be generated from said first CT data, said first CT data being obtained from a polychromatic scan, said second CT data comprising first data corresponding to a first parameter and second data corresponding to a second parameter for a given volume, wherein said first parameter and said second parameter correspond to projection-based reconstructions of monochromatic images showing effects of attenuation for an object as if the object were scanned by a monochromatic source instead of a polychromatic source; and
a processing routine configured to generate a scatter plot based on said first and second data, wherein said first data corresponds to a first axis and said second data corresponds to a second axis, said processing routine configured to identify at least one material type based on said scatter plot.

16. The computer-readable medium of claim 15 further comprising a user interface routine configured to provide a user with the option to select a portion of an image representing scanned anatomy for which said scatter plot will be generated.

17. The computer-readable medium of claim 15 wherein said processing routine is configured to identify a plurality of material types based on clusters identified in said scatter plot.

18. The computer-readable medium of claim 15, wherein said first data comprises Hounsfield unit values corresponding to a first energy level, and said second data comprises Hounsfield unit values corresponding to a second energy level.

19. The computer-readable medium of claim 15, further comprising a display routine configured to allow displaying an image representative of scanned anatomy including at least one material type identified based on said scatter plot for at least a portion of said image.

20. The computer-readable medium of claim 15 further comprising a parameter selection routine configured to allow a user to select said first and second parameters.

* * * * *